United States Patent [19]

Ogata et al.

[11] Patent Number: 5,097,074

[45] Date of Patent: Mar. 17, 1992

[54] PROCESS FOR PURIFYING 4,4'-DIHYDROXYDIPHENYLSULFONE

[75] Inventors: Eiji Ogata; Koji Ono, both of Wakayama, Japan

[73] Assignee: Konishi Chemical Industry, Limited, Wakayama, Japan

[21] Appl. No.: 362,411

[22] PCT Filed: Aug. 17, 1988

[86] PCT No.: PCT/JP88/00813

§ 371 Date: Apr. 10, 1989

§ 102(e) Date: Apr. 10, 1989

[87] PCT Pub. No.: WO89/01469

PCT Pub. Date: Feb. 23, 1989

[30] Foreign Application Priority Data

Aug. 21, 1987 [JP] Japan .................. 62-208434
Aug. 21, 1987 [JP] Japan .................. 62-208435
Jan. 22, 1988 [JP] Japan .................. 63-13313

[51] Int. Cl.$^5$ .................. C07C 315/06
[52] U.S. Cl. .................. 568/33
[58] Field of Search .................. 568/33

[56] References Cited

U.S. PATENT DOCUMENTS 2,392,137  1/1946  Foster .................. 568/33
3,277,183 10/1966  Heller et al. .................. 568/33
3,297,766  1/1967  Bradley et al. .................. 568/33
4,162,270  7/1979  Ogata et al. .................. 568/33

FOREIGN PATENT DOCUMENTS 220855  5/1987  European Pat. Off. .......... 568/33
93271   4/1987  Japan .................. 568/33
956468  9/1982  U.S.S.R. .................. 568/33

OTHER PUBLICATIONS

G. Hawley, The Condensed Chemical Dictionary, Tenth Edition (1981), p. 907, Van Nostrand Reinhold Co., N.Y.

Primary Examiner—John M. Ford
Attorney, Agent, or Firm—Armstrong, Nikaido, Marmelstein, Kubovcik & Murray

[57] ABSTRACT

The invention provides a process for purifying crude 4,4'-dihydroxydiphenylsulfone characterized by dissolving the crude 4,4'-dihydroxydiphenylsulfone in an aqueous solution of a basic substance, precipitating a mono-salt of 4,4'-dihydroxydiphenylsulfone from the resulting solution by salting out, separating the salt off and subsequently treating the salt with an acid, and also porovides a process for preparing a mono-salt of 4,4'-dihydroxydiphenylsulfone characterized by dissolving crude 4,4'-dihydroxydiphenylsulfone in an aqueous solution of a basic substance, precipitating a mono-salt of 4,4'-dihydroxydiphenylsulfone from the resulting solution by salting out, and separating the salt off.

7 Claims, No Drawings

PROCESS FOR PURIFYING 4,4'-DIHYDROXYDIPHENYLSULFONE

TECHNICAL FIELD

The present invention relates to a novel process for purifying crude 4,4'-dihydroxydiphenylsulfone to obtain 4,4'-dihydroxydiphenylsulfone of high purity in a high yield, and to a novel process for preparing an intermediate of purification by the purifying process.

BACKGROUND ART 4,4'-Dihydroxydiphenylsulfone (hereinafter referred to as "4,4'-compound") is excellent in resistance to heat and oxidation, stability to light, etc. and has therefore found wide use in recent years in the field of the high polymer industry relating to polyester resin, epoxy resin, polycarbonate resin, polyether sulfone resin and the like. When high-polymer products are prepared from 4,4'-compound containing impurities such as 2,4'-dihydroxydiphenylsulfone (hereinafter referred to as "2.4'-compound") and trihydroxytriphenyldisulfone (hereinafter referred to as "tri-compound"), the products tend to have a decreased molecular weight and impaired mechanical properties. This tendency becomes more pronounced when 2,4'-compound, tri-compound and like impurities are present in larger quantities. Accordingly, it has been desired to supply 4,4'-compound of high purity free from the impurities such as 2,4'-compound and tri-compound to the greatest possible extent 4,4'-Compound is useful also as a material for couplers for color photography, as a color developer for heat-sensitive recording paper, etc., and a high purity is also desirable in such uses.

Industrially, 4,4'-compound is prepared primarily by the dehydration reaction of phenol with a sulfonating agent such as sulfuric acid. The reaction mixture contains 2,4'-compound, tri-compound and like sulfones, other sulfonic acids, etc. as impurities. When sulfonic acids, etc. are removed from the reaction mixture, the resulting crude 4,4'-compound usually contains about 70 to about 80 wt. % of 4,4'-compound.

Processes have been developed for preparing 4,4'-compound of high purity by inhibiting formation of 2,4'-compound. For example, a process for producing 4,4'-compound of high purity is proposed wherein 4,4'-compound is produced by a dehydration reaction while effecting precipitation of the product and isomerization of 2,4'-compound, a by-product, to 4,4'-compound (U.S. Pat. No. 4,162,270). The crude 4,4'-compound obtained by removing sulfonic acids and the like from the reaction mixture of this process usually contains about 90 to about 95 wt. %. Nevertheless, it is desired that the 4,4'-compound for the various uses mentioned above be at least about 97 wt. % in purity, for example, because higher qualities are required of resins in recent years. Accordingly, the compound prepared by the former process must be further purified, and the compound obtained by the latter process should preferably be further purified.

Processes for purifying 4,4'-compound have been proposed which employ various organic solvent mixtures, such as o-dichlorobenzene-phenol (Examined Japanese Patent Publication SHO 51-36264), o-dichlorobenzene-acetic acid (Examined Japanese Patent Publication SHO 57-48152), o-dichlorobenzene-ethyl acetate (Examined Japanese Patent Publication SHO 57-48153) and o-dichlorobenzene-alcohol (Examined Japanese Patent Publication SHO 58-2234). However, these processes all use organic solvents and accordingly have the problem that the solvents are inconvenient to handle and hazardous from the viewpoint of sanitation and cause environmental pollution.

Alternatively without using organic solvents, 4,4'-compound is usually purified by dissolving crude 4,4'-compound in an aqueous solution of sodium hydroxide or like alkali, treating the solution with active carbon and thereafter adding an acid, such as sulfuric acid, to the solution in an amount at least sufficient to neutralize the solution to precipitate 4,4'-compound. This process utilizes the properties of 4,4'-compound that it is sparingly soluble in water but readily soluble in aqueous solutions of basic substances in the form of a mono- or di-metal salt of the compound. This process removes sulfonic acids but almost fails to remove 2,4'-compound, tri-compound and like sulfones, giving a product of a low purity which is in no way as high as is desired as will be apparent from the comparative example given later.

DISCLOSURE OF THE INVENTION

An object of the invention is to provide a novel purifying process for producing 4,4'-compound of high purity in a high purification yield (yield based on the content of 4,4'-compound in the crude) without using organic solvents in order to fully fulfill the foregoing requirement.

Another object of the invention is to provide a novel process for producing a purification intermediate in a high yield by the above process for purifying 4,4'-compound.

These and other objects of the invention will become apparent from the following description.

The present invention provides a process for purifying crude 4,4'-compound characterized by dissolving the crude 4,4'-compound in an aqueous solution of a basic substance, precipitating a mono-salt of 4,4'-compound from the resulting solution by salting out, separating the salt off and subsequently treating the salt with an acid.

The invention further provides a process for preparing a mono-salt of 4,4'-compound characterized by dissolving crude 4,4'-compound in an aqueous solution of a basic substance, precipitating a mono-salt of 4,4'-compound from the resulting solution by salting out, and separating the salt off.

To fulfill the above objects, we have conducted intensive research and consequently obtained the unique finding that when crude 4,4'-compound is dissolved in an aqueous solution of a basic substance and thereafter subjected to salting out, a mono-metal salt, mono-ammonium salt or like mono-salt of 4,4'-compound corresponding to the basic substance used can be obtained with a high purity. We have further found that the salt, when subsequently treated with an acid, gives 4,4'-compound having a high purity of at least 99 wt. % usually in a high purification yield of at least about 85%. The fact that 4,4'-compound can be salted out as a mono-salt of high purity under a specified condition is totally unexpected by one skilled in the art resorting to the common knowledge that mono- or di-metal salts or mono- or diammonium salt of 4,4'-compound is readily soluble in water. The present invention has been accomplished based on the above novel findings.

The term "mono-metal salt" as used herein refers to a mono-alkali metal salt, mono ½ alkaline earth metal salt or the like.

The processes of the invention are usable for purifying crudes of 4,4'-compound of any purity including reaction mixtures for preparing 4,4'-compound, such mixtures free from sulfonic acids, etc., and commercial products of 4,4'-compounds.

According to the present invention, crude 4,4'-compound is first dissolved in an aqueous solution of a basic substance usually with stirring. Examples of useful basic substances are hydroxides, carbonates or the like of alkali metals such as sodium and potassium, and alkaline earth metals such as magnesium and calcium and ammonia. Especially preferable among these are sodium hydroxide, sodium carbonate and ammonia.

The concentration of the aqueous solution of basic substance is not limited specifically but is determined suitably in accordance with the amounts of basic substance and water to be used. To be suitable, the amount of basic substance to be used is the amount needed to neutralize the sulfonic acids and like strong acids present, plus approximately at least one equivalent to not greater than 2 equivalents per mole of sulfones such as 4,4'-compound, 2,4'-compound and tri-compound. When the amount is less than the above range, free 4,4'-compound becomes mixed with the mono-metal salt or monoammonium salt of 4,4'-compound salted out to give crystals of impaired form and result in a lower effect to remove the impurities, hence objectionable. When a salting-out agent is added directly to the solution of the crude compound containing the basic substance in an amount exceeding the above range, a di-metal salt or diammonium salt of 4,4'-compound which is not salted out is formed in a large amount to result in an undesirable tendency toward a lower yield. However, use of more than two equivalents of the basic substance per mole of 4,4'-compound and like sulfones is not substantially in any way objectionable but is an advantageous mode of practicing the invention. More specifically, when more than 2 equivalents of the basic substance is used excessively to obtain a solution containing a large amount of di-metal salt or diammonium salt of 4,4'-compound each formed therein and incapable of being salted out, the solution can be treated favorably with active carbon or the like when so required. An acid is then added to the solution to convert the di-salt to a mono-salt and to form a salting-out agent at the same time, followed by further addition of salting-out agent when required, whereby the mono-salt can be salted out.

When the crude 4,4'-compound is added to the aqueous solution obtained by the dissolving step, the resulting liquid is in the form of a solution or suspension depending on the amount of the basic substance or water. In the case of the suspension, the liquid phase generally contains a mono-metal salt or monoammonium salt of 4,4'compound and a small amount of di-metal salt or diammonium salt of 4,4'-compound dissolved therein, and the solid phase is composed predominantly of the mono-salt of 4,4'-compound separating out upon oversaturation of the aqueous solution after dissolving the 4,4'-compound therein. Presumably, the mono-salt of 4,4'-compound further separates out from the liquid phase through salting out to give grown crystals.

Although the amount of water to be used for the dissolving step is variable widely, it is suitable to use usually about 1.0 to about 8.0 times the amount by weight of the crude 4,4'-compound. If the amount of water is smaller than this range, a suspension will be formed which contains a large proportion of solid phase to exhibit low fluidity and tends to become difficult to stir, whereas a larger amount of water, if used, results in a tendency toward a decreased purification yield. Thus, amounts outside the range are not desirable. It is especially desirable to use water in about 1.3 to about 3.0 times the amount by weight of the crude 4,4'-compound.

The temperature for the dissolving step, although not limited specifically, is favorably about 40° C. to the boiling point since the mono-metal salt or monoammonium salt of 4,4'-compound can then be formed at an increased velocity.

The solution or suspension obtained above by treating the crude 4,4'-compound is subjected to a salting-out step usually with stirring to precipitate the mono-metal salt or monoammonium salt of 4,4'-compound. This step precipitates the mono-metal salt or monoammonium salt of 4,4'-compound usually with a high purity of about 98 wt. % or more in a high yield of about 86% or more based on the 4,4'-compound in the crude. We have found this fact for the first time.

The salting-out step is executed by adding a salting-out agent to the solution or suspension, or using an excess of the basic substance and adding hydrochloric acid, sulfuric acid or like acid to the solution or suspension to form a salting-out agent, or by the combination of these methods. Examples of preferred salting-out agents are chlorides, sulfates or the like of alkali metals, such as sodium and potassium, and alkaline earth metals such as calcium and magnesium, and ammonium salts such as ammonium chloride and ammonium sulfate From the viewpoint of purification yield, purity, etc., it is desirable to use a salting-out agent which is a salt corresponding to the basic substance used. The amount of salting-out agent to be used is variable over a wide range. Generally, it is suitable to use the agent in an amount not less than 2 wt. % to the saturation concentration in terms of concentration. If the amount is smaller than this range, a lower salting-out effect and a reduced yield will result, whereas amounts exceeding the saturation concentration permit crystals of the salting-out agent to separate out. Amounts outside the above range are therefore undesirable. It is usually desirable to use the salting-out agent in an amount of about 4 to about 15 wt. %.

The temperature at which the salting-out agent is to be added to the solution or suspension, although not limited specifically, is favorably about 40° C. to the boiling point, since the mono-metal salt or monoammonium salt of 4,4'-compound can be obtained in an improved form of crystals, with an improved purity and in a higher yield. After addition of the salting-out agent, the mixture may be aged at this temperature for about 0.2 to about 12 hours.

The mono-metal salt or monoammonium salt of 4,4'-compound precipitated is then separated off as by filtration and suitably washed as required to give the mono-salt of 4,4'-compound having a high purity. Usually, the salt is subsequently treated with an acid to obtain free 4,4'-compound. The acid treatment is conducted in the usual manner, i.e., by dissolving the mono-metal salt or monoammonium salt of 4,4'-compound in water or an aqueous alkali solution, treating the solution with active carbon when required, then adjusting the pH to about 3 to about 6 with sulfuric acid, hydrochloric acid or like acid to precipitate 4,4'-compound and separating off the precipitate as by filtration. This method affords the compound substantially quantitatively.

In this way, the desired 4,4'-compound can be obtained with a high purity in a high purification yield.

The high-purity mono-metal salt or monoammonium salt of 4,4'-compound prepared by the above process can be used as it is as an industrial material depending on the use.

The processes of the invention have the outstanding advantages given below.

(1) The process wherein no organic solvent is used can be practiced by a facilitated procedure and poses no problem in respect of sanitation and environment.

(2) The process usually affords 4,4'-compound with a high purity of at least 99 wt. % in a high purification yield of at least 85%, thus fully satisfying the demand of the industry.

(3) The process purifies a larger amount of crude with use of a reduced amount of liquid more efficiently than the conventional processes and can be practiced by compact equipment with a high work efficiency.

BEST MODE OF CARRYING OUT THE INVENTION

The invention will be described in greater detail with reference to the following reference example, examples and comparative example.

REFERENCE EXAMPLE 1

Crude 4,4'-compound was prepared by the process of U.S. Pat. No. 4,162,270.

More specifically, a mixture of 290 g of phenol, 146 g of 98 wt. % sulfuric acid and 150 g of o-dichlorobenzene (ODCB) was heated with stirring. At about 150° C., the mixture started to boil and to distill off ODCB and water formed on reaction. The distillate was condensed, with the ODCB phase continuously returned to the reaction system. After the amount of the water layer reached 52 ml, the reaction temperature was maintained at 175 to 185° C., and the resulting water and ODCB containing a small amount of phenol were distilled off for recovery in an adjusted vacuum over a period of 4 hours until the reaction product was solidified to dryness.

When analyzed by high performance liquid chromatography, the dry reaction product was found to contain 84.6 wt. % of 4,4'-compound, 2.0 wt. % of 2,4'-compound, 4.5 wt. % of tri-compound and 8.9 wt. % of other sulfonic acids, etc.

EXAMPLE 1

A 100-gram portion of the dry reaction product, i.e. crude 4,4'-compound obtained in Reference Example 1, was added to 155 g of water and 18.1 g of sodium hydroxide (the sum of the amount required for neutralizing the sulfonic acids and the amount corresponding to 1.2 times the equivalent based on the total amount of the sulfones including 4,4'-compound, 2,4'-compound and tri-compound). The mixture was heated to 95° C. with stirring. The product did not dissolve completely, forming a suspension.

With addition of 10 g of sodium chloride, the suspension was then maintained at the same temperature for 30 minutes for aging and thereafter cooled. After maintaining the mixture at 50° C. for 1 hour, the resulting precipitate was filtered off and washed with 50 ml of 5 wt. % aqueous solution of sodium chloride, giving 84.0 g of monosodium salt of 4,4'-compound (purification yield 91.3%).

The monosodium salt of 4,4'-compound obtained was treated with hydrochloric acid and thereafter analyzed by high performance liquid chromatography, with the result given in Table 1.

The monosodium salt of 4,4'-compound obtained was dissolved in 900 ml of water and 78 wt. % of sulfuric acid was added to the solution at a temperature of 90 to 95° C. to adjust the solution to a pH of 4.0 and precipitate 4,4'-compound. After cooling the reaction mixture to 40° C., the precipitate was filtered off and dried, giving 76.6 g of purified 4,4'-compound in a purification yield of 90.4% (based on the content of 4,4'-compound in the crude).

Table 1 shows the result obtained by analyzing the purified product by high performance liquid chromatography.

EXAMPLE 2

The same salting-out step as in Example 1 was repeated with the exception of using 15 g of anhydrous sodium sulfate in place of 10 g of sodium chloride serving as the salting-out agent in Example 1, giving 83.2 g of monosodium salt of 4,4'-compound (purification yield 90.4%). The salt was similarly treated with sulfuric acid to obtain 75.9 g of purified 4,4'-compound.

The purification yield was 89.5%. The purified product was analyzed by high performance liquid chromatography, with the result shown in Table 1.

EXAMPLE 3

A 100-gram portion of the dry reaction product, i.e. crude 4,4'-compound, obtained in Reference Example 1, was added to 280 g of water and 31.6 g of sodium hydroxide (the sum of the amount required for neutralizing the sulfonic acids and the amount corresponding to 2.1 times the equivalent based on the sulfones such as 4,4'-compound). The mixture was heated to 95° C. with stirring, whereby the product was completely dissolved.

Next, 24.1 g of 78 wt. % sulfuric acid was slowly added to the solution, which was then cooled to 50° C. and maintained at this temperature for 1 hour. The crystals separating out were filtered off and washed with 5 wt. % aqueous solution of sodium sulfate, giving 81.0 g of monosodium salt of 4,4'-compound (purification yield 88.0%).

The monosodium salt of 4,4'-compound obtained was analyzed by high performance liquid chromatography. Table 1 shows the composition of the salt thus determined.

The monosodium salt of 4,4'-compound obtained was treated with sulfuric acid in the same manner as in Example 1, affording 73.9 g of purified 4,4'-compound. The purification yield was 87.3%. Table 1 shows the result obtained by analyzing the product by high performance liquid chromatography.

EXAMPLE 4

A commercial crude product of 4,4'-compound was analyzed by high performance liquid chromatography to find that the product contained 82.6 wt. %, 14.0 wt. % and 3.4 wt. % of 4,4'-compound, 2,4'-compound and tri-compound, respectively.

The crude product (100 g) was added to 160 g of water and 33.2 g of sodium hydroxide (2.1 times the equivalent based on the total amount of the sulfones such as 4,4'-compound), and the mixture was heated to 97° C. with stirring. The product did not dissolve completely, giving a suspension.

Next, 25.1 g of 78 wt. % sulfuric acid was slowly added to the suspension, the mixture was cooled and maintained at 50° C. for 1 hour, and the crystals separating out were filtered off and washed with 5 wt. % aqueous solution of sodium sulfate to obtain 80.4 g of monosodium salt of 4,4'-compound (purification yield 87.4%).

The monosodium salt of 4,4'-compound obtained was analyzed by high performance liquid chromatography. Table 1 shows the composition of the salt thus determined.

The monosodium salt of 4,4'-compound obtained was treated in the same manner as in Example 1, affording 71.5 g of purified 4,4'-compound in a purification yield of 85.8 wt. %. Table 1 shows the result obtained by subjecting the purified product to high performance liquid chromatography.

TABLE 1

|  | 4,4'-Compd. (wt. %) | 2,4'-Compd. (wt. %) | Tri-Compd. (wt. %) |
|---|---|---|---|
| Example 1 |  |  |  |
| Monosodium salt | 99.43 | 0.25 | 0.16 |
| Purified product | 99.88 | 0.09 | 0 |
| Example 2 |  |  |  |
| Monosodium salt | 99.39 | 0.26 | 0.18 |
| Purified product | 99.87 | 0.09 | 0.01 |
| Example 3 |  |  |  |
| Monosodium salt | 99.60 | 0.15 | 0.10 |
| Purified product | 99.92 | 0.05 | 0 |
| Example 4 |  |  |  |
| Monosodium salt | 98.00 | 1.28 | 0.42 |
| Purified product | 99.08 | 0.65 | 0.05 |

EXAMPLE 5

A 100-gram portion of the dry reaction product, i.e. crude 4,4'-compound, obtained in Reference Example 1, was added to 135 g of water and 27.5 g of ammonia water containing 28 wt. % of ammonia (the sum of the amount required for neutralizing the sulfonic acids and the amount corresponding to 1.2 times the equivalent based on the total amount of the sulfones, i.e. 4,4'-compound, 2,4'-compound and tri-compound). The mixture was heated to 95° C. with stirring. The product did not dissolve completely, forming a suspension.

With addition of 20 g of ammonium sulfate, the suspension was then maintained at the same temperature for 30 minutes for aging and thereafter cooled. After maintaining the mixture at 50° C. for 1 hour, the resulting precipitate was filtered off and washed with 50 ml of 5 wt. % aqueous solution of ammonium sulfate, giving 80.8 g of monoammonium salt of 4,4'-compound (purification yield 89.4%).

The monoammonium salt of 4,4'-compound obtained was treated with hydrochloric acid and thereafter analyzed by high performance liquid chromatography, with the result listed in Table 2.

The monoammonium salt of 4,4'-compound obtained was dissolved in 900 ml of water, and 78 wt. % of sulfuric acid was added to the solution at a temperature of 90 to 95° C. to adjust the solution to a pH of 4.0 and precipitate 4,4'-compound. After cooling the reaction mixture to 40° C., the precipitate was filtered off and dried, affording 74.9 g of purified 4,4'-compound in a purification yield of 88.5% (based on the content of 4,4'-compound in the crude).

The product was analyzed by high performance liquid chromatography. Table 2 shows the result.

EXAMPLE 6

A 100-gram portion of the dry reaction product, i.e. crude 4,4'-compound, obtained in Reference Example 1, was added to 200 g of water and 48.0 g of ammonia water containing 28 wt. % of ammonia (the sum of the amount required for neutralizing the sulfonic acids and the amount corresponding to 2.1 times the equivalent based on the sulfones such as 4,4'-compound). The mixture was heated to 95° C. with stirring. The product did not dissolve completely, forming a suspension.

Next, 24.1 g of 78 wt. % sulfuric acid was slowly added to the suspension, the mixture was then cooled and maintained at 50° C. for 1 hour, and the crystals separating out were filtered off and washed with 50 ml of 5 wt. % aqueous solution of ammonium sulfate, affording 77.7 g of monoammonium salt of 4,4'-compound (purification yield 86.0%).

The monoammonium salt of 4,4'-compound obtained was analyzed by high performance liquid chromatograhy. Table 2 shows the composition of the salt thus determined.

The monoammonium salt of 4,4'-compound obtained was treated with sulfuric acid in the same manner as in Example 5, affording 72.1 g of purified 4,4'-compound in a purification yield of 85.2%. The purified product was analyzed by high performance liquid chromatography. Table 2 shows the result.

TABLE 2

|  | 4,4'-Compd. (wt. %) | 2,4'-Compd. (wt. %) | Tri-Compd. (wt. %) |
|---|---|---|---|
| Example 5 |  |  |  |
| Monoammonium salt | 99.23 | 0.20 | 0.25 |
| Purified product | 99.87 | 0.04 | 0 |
| Example 6 |  |  |  |
| Monoammonium salt | 99.49 | 0.12 | 0.18 |
| Purified product | 99.94 | 0.02 | 0 |

COMPARATIVE EXAMPLE 1

A 100-gram portion of the crude 4,4'-compound prepared in Reference Example 1, 31.6 g of sodium hydroxide and 280 g of water were stirred at an elevated temperature to prepare a solution, 48.0 g of 78 wt. % sulfuric acid was added to the solution at 95° C. to adjust the solution to a pH of 4, and the mixture was cooled and maintained at 50° C. for 1 hour. The resulting precipitate was filtered off and dried, giving 89.9 g of 4,4'-compound in a yield of 99.3%. When analyzed by high performance liquid chromatography, the product was found to contain 93.4 wt. % of 4,4'-compound, 1.7 wt. % of 2,4'-compound and 4.9 wt. % of tri-compound.

We claim:

1. A process for purifying crude 4,4'-dihydroxydiphenylsulfone comprising adding said crude 4,4'-dihydroxydiphenylsulfone to an aqueous solution of a basic substance whereby forming a salt of said sulfone with the cation of said basic substance; adding a different soluble salt to said aqueous solution in an amount and under conditions whereby precipitating a mono-salt of 4,4'-dihydroxydiphenylsulfone from the resulting solution; separating the precipitated salt from the remaining aqueous phase; and subsequently treating the separated salt with an acid in an amount and under conditions whereby forming purified 4,4'-dihydroxydiphenylsulfone.

2. A process as defined in claim 1 wherein the basic substance is a hydroxide or a carbonate of an alkali metal or an alkaline earth metal, or ammonia.

3. A process as defined in claim 1 wherein the mono-salt of 4,4'-dihydroxydiphenylsulfone is a monoalkali metal salt, a mono ½ alkaline earth metal salt or mono-ammonium salt thereof.

4. A process as defined in claim 1 wherein said crude 4,4'-dihydroxydiphenylsulfone is dissolved in about 1.0 to about 8.0 times its weight in water.

5. A process for preparing a mono-salt of 4,4'-dihydroxydiphenylsulfone comprising dissolving crude 4,4'-dihydroxydiphenylsulfone in an aqueous solution of a basic substance; precipitating a mono-salt of 4,4'-dihydroxydiphenylsulfone from the resulting solution by salting out, and separating the precipitated salt.

6. A process as defined in claim 5 wherein the basic substance is a hydroxide or a carbonate of an alkali metal or an alkaline earth metal, or ammonia.

7. A process as defined in claim 5 wherein the mono-salt of 4,4'-dihydroxydiphenylsulfone is a monoalkali metal salt, mono ½ alkaline earth metal salt a or a mono-ammonium salt thereof.

* * * * *